United States Patent
Dietzel et al.

(10) Patent No.: US 7,066,881 B2
(45) Date of Patent: Jun. 27, 2006

(54) SPREADING LARYNGOSCOPE

(75) Inventors: Daniel Dietzel, Kelkheim (DE); Helmut Heckele, Knittlingen (DE)

(73) Assignee: Richard Wolf GmbH, Knittlingen (DE)

( * ) Notice: Subject to any disclaimer, the term of this patent is extended or adjusted under 35 U.S.C. 154(b) by 331 days.

(21) Appl. No.: 10/426,214

(22) Filed: Apr. 30, 2003

(65) Prior Publication Data

US 2003/0212309 A1    Nov. 13, 2003

(30) Foreign Application Priority Data

May 7, 2002    (DE) .............................. 102 20 497

(51) Int. Cl.
*A61B 1/267*    (2006.01)

(52) U.S. Cl. .................................. 600/190

(58) Field of Classification Search ............... 600/185, 600/186, 190, 193, 194, 195, 210, 217, 218, 600/220, 222, 237, 239, 240; 269/147; 132/277, 132/276, 279, 231, 224, 225; 24/564

See application file for complete search history.

(56) References Cited

U.S. PATENT DOCUMENTS

| | | | |
|---|---|---|---|
| 5,868,668 A | 2/1999 | Weiss | |
| 6,095,972 A | 8/2000 | Sakamoto | |
| 6,357,089 B1 * | 3/2002 | Koguchi et al. | 24/536 |
| 6,647,990 B1 * | 11/2003 | Shinn | 132/224 |
| 2003/0056344 A1 * | 3/2003 | Brogdon, III | 24/564 |

FOREIGN PATENT DOCUMENTS

| | | |
|---|---|---|
| DE | 199 54 442 A1 | 6/2001 |
| SE | 466 379 B | 2/1992 |
| WO | WO 98/33431 A1 | 8/1998 |
| WO | WO 01/34019 A1 | 5/2001 |
| WO | WO 03/032821 A1 | 4/2003 |

* cited by examiner

*Primary Examiner*—Eduardo C. Robert
*Assistant Examiner*—Michael J. Araj
(74) *Attorney, Agent, or Firm*—Akin Gump Strauss Hauer & Feld, LLP

(57) ABSTRACT

A spreading laryngoscope is provided with two spatulas able to be moved apart, wherein on at least on of the two spatulas on each longitudinal side there is formed at least one projecting tab. The at least one tab on each side proceeds from the longitudinal side of the one spatula, extends to the other spatula, and is rigidly connected to the one spatula from which it proceeds.

11 Claims, 2 Drawing Sheets

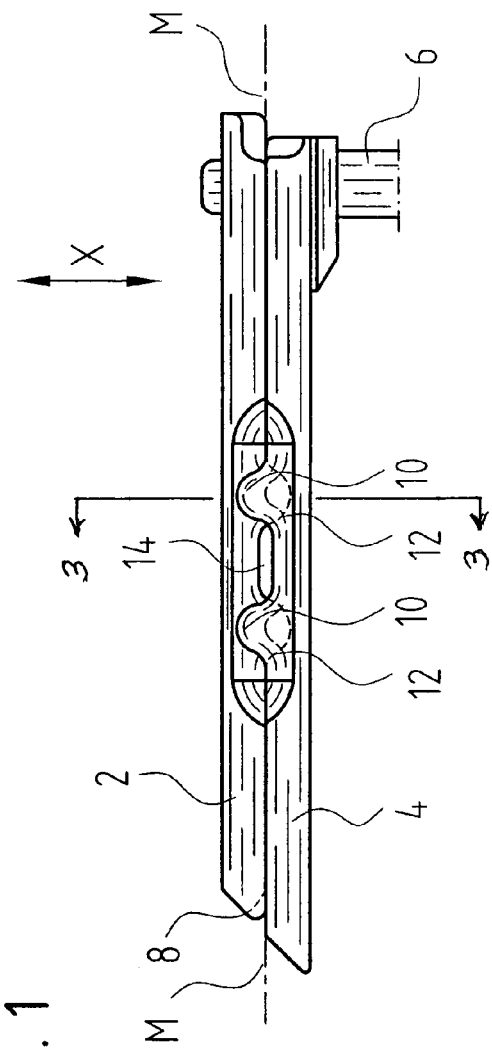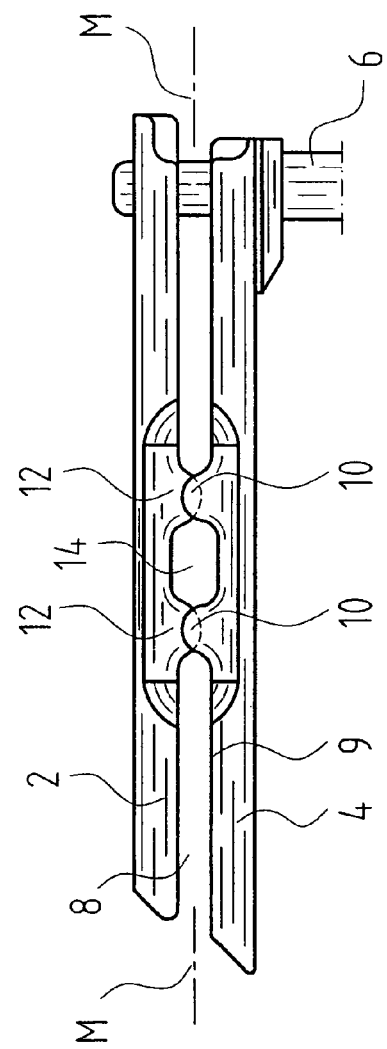

SPREADING LARYNGOSCOPE

BACKGROUND OF THE INVENTION

The invention relates to a spreading laryngoscope.

Spreadable laryngoscopes are known which comprise two spatulas parallel to one another, which delimit a working space through which instruments may be introduced in order to carry out an operation. Such a laryngoscope is known, for example, from German Published Patent Application DE 199 54 442 A1. This laryngoscope comprises two spatulas which are connected to a grip part. On the grip part there is provided an adjusting mechanism by which the two spatulas may be spread. At the same time, the spatulas are adjusted in parallel or angularly, so that they are further spaced from one another, in order to create a larger working space. At the same time, lateral gaps arise between the two longitudinal sides of the spatulas. According to DE 199 54 442 A1, movable flaps are arranged on a spatula in order to close the lateral gap in the spread condition and prevent tissue from penetrating into the gap. The arrangement of the movable flaps has the disadvantage that the field of view for the operator into the laterally retracted tissue is greatly limited, and additionally the outer dimensions of the laryngoscope are increased on account of the pivotable flaps.

BRIEF SUMMARY OF THE INVENTION

It is the object of the invention to create an improved spreading laryngoscope which is designed more compactly and permits an improved protection of soft parts and organs, in particular with operations in the region of the larynx/pharynx, and also permits an enlarged field of view to the operator.

A spreading laryngoscope achieves this object with two spatulas (2,4) lying opposite one another and able to be moved apart, at least one of the two spatulas (2, 4) having on each longitudinal side thereof at least one projecting tab (10, 12), the at least one projecting tab (10, 12) on each longitudinal side proceeding from the respective longitudinal side of the one spatula (2,4), extending to the opposite-lying spatula (2, 4), and being rigidly connected to the spatula (2, 4) from which it proceeds. Preferred embodiments are set forth below and in the dependent claims.

The spreading laryngoscope according to the invention comprises two spatulas which may be moved apart, as with known laryngoscopes. The two spatulas are preferably fixed in a common grip part and may be moved apart parallel to one another or at an angle to one another in order to create an enlarged working space between the spatulas. According to the invention, on at least one of the two spatulas on each of its longitudinal sides there is in each case provided at least one projecting tab or a projecting projection, which in each case extends from the respective longitudinal side of the one spatula in the direction of the other spatula. At the same time, the tabs are rigidly connected to the respective spatula on its longitudinal sides. This rigid connection of the tabs permits a more compact design of the laryngoscope than with the use of pivotable flaps. One further achieves a more economical manufacture and a greater durability.

The tabs or projections at least partly cover over sections of the lateral gaps, which arise when the two spatulas are moved apart. At the same time, the tabs at least partly cover or bridge the lateral gaps between the spatulas, in the transverse direction, i.e. essentially normal to the main spatula surfaces, in order to prevent a penetration of tissue into the spaces between the spatulas. Preferably, the tabs do not extend over the whole length of the spatula, but only over short sections in the longitudinal direction of the spatula, so that a large region of the lateral gaps between the spatulas is not covered by the tabs, by which means one creates a large field of view for the operator.

According to a preferred embodiment, on each of the two spatulas on each respective longitudinal side of the spatula, there is formed at least one projecting tab which proceeds from the longitudinal side of the one spatula, extends towards the other spatula, and is rigidly connected to the spatula. According to this arrangement, the arising gap may be safely protected from penetrating tissue even with a greater spacing between the spread spatulas. The arrangement of projections on the two spatulas at the same time, with the use of rigid projections, also permits the bridging or covering of wider gaps between the spatulas in a transverse direction, in particular normal to the longitudinal direction of the spatula.

Preferably, the tabs formed on the two spatulas are arranged lying opposite to one another in a manner such that a tab on a first spatula overlaps with a tab on the second spatula at least in a non-spread condition of the laryngoscope. With this arrangement the two tabs lying opposite one another on the two spatulas form a common closed section which bridges the lateral gap or free space between the two spatulas, in order to prevent a penetration of tissue structures and organ parts. At the same time, the two tabs overlapping one another form a web between the two spatulas. By way of the overlapping design, one may also bridge a larger gap or free space between the two spatulas. Since the web formed by the tabs extends only over a narrow region in the longitudinal direction of the spatula, the larger part of the spatula preferably remains uncovered, by which means a good lateral view is made possible.

The tabs further preferably extend essentially normally to the main surfaces of the spatula. The main surfaces of the spatula are, however, the surfaces of the two spatulas extending in the longitudinal direction, i.e., the actual spatula surfaces which lie opposite one another and form the upper and lower sides of the laryngoscope. This means the tabs extend essentially parallel to the movement direction of the two spatulas when these are moved apart or towards one another. The tabs overlapping one another, at the same time, preferably extend parallel to one another, so that the inner side of the one tab bears on the outer side of the other tab or extends at a slight spacing parallel to this. Thus, a closed web is formed which may prevent the penetration of soft material or tissue parts. The arrangement of the tabs parallel to the movement direction of the spatulas permits a large adjustment path of the two spatulas to one another without this path being limited by the arrangement of the tabs.

On at least one longitudinal side of each of the two spatulas there are formed two respective tabs, which in the non-spread condition of the laryngoscope overlap with two oppositely lying tabs on the respective other spatula. Due to the fact that two tabs are provided on at least one and preferably on each longitudinal side, one may even more reliably prevent a penetration of tissue. Simultaneously, the arrangement of two individual tabs, in contrast to one larger tab, has the advantage that the field of view to the operator is less restricted, since the tabs only form narrow webs between the spatulas, the remaining part of the spatula however remaining free in order to ensure a sufficient lateral view.

The two tabs on each side are preferably spaced from one another in the longitudinal direction of the spatula. Thus, a free space between the two tabs arises which permits an improved view of tissue lying laterally of the spatula during an operation. Simultaneously, the tabs spaced from one another may ensure that soft parts or tissue parts do not penetrate into the gap between the two spatulas.

It is further preferred for the tabs to be designed such that in each case they overlap with an oppositely lying tab on the respective other spatula, even in the spread condition of the laryngoscope. This also means that in each spread position of the two spatulas, the oppositely lying tabs overlap such that a continuous closed web is formed between the two spatulas, in order to prevent a penetration of tissue parts into the gap between the two spatulas. At the same time, however, the tabs in the longitudinal direction of the spatulas do not extend over the whole length of the spatulas, so that the view to tissue parts lying laterally of the laryngoscope is restricted as little as possible. The laryngoscope may, however, alternatively be designed and applied such that the spatulas are spaced or spread further from one another, so that the tabs lying opposite one another on both spatulas no longer overlap and a gap arises between the end faces of the tabs. This gap is, however, considerably narrower than the remaining arising gap between the two spatulas, so that even with such an arrangement, one may prevent a penetration of tissue structures into the respective lateral gap between the two spatulas. At the same time, the lateral view is limited as little as possible.

Preferably the tabs are designed as one piece with the respective associated spatula. For example, the tabs may be manufactured together with the associated spatula of a metal (sheet) plating by way of suitable cutting and non-cutting shaping. This permits an inexpensive manufacture of the laryngoscope.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIG. 1 is a lateral view of the laryngoscope according to the invention, in the non-spread condition, FIG. 2 is a lateral view of the laryngoscope of FIG. 1, in the spread condition.

DETAILED DESCRIPTION OF THE INVENTION

Figure 3:
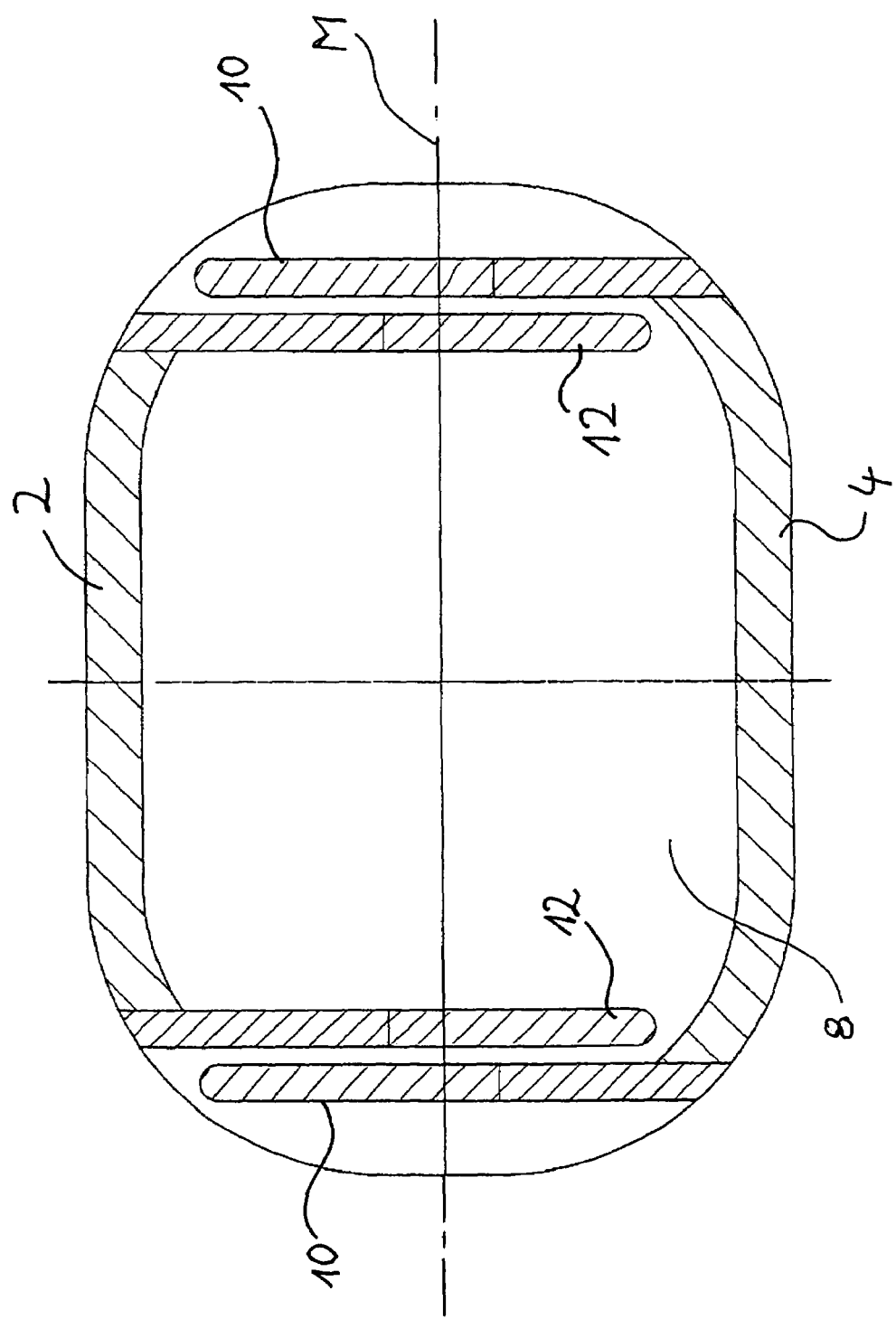
FIG. 3 is a cross-sectional view of the laryngoscope of FIG. 1, taken along section line 3—3.

The laryngoscope according to the invention and according to a preferred embodiment form is first explained in the non-spread condition by way of FIG. 1. The laryngoscope, as with known spreading laryngoscopes, has two spatulas 2 and 4 extending parallel to one another. The spatulas 2 and 4 are connected to one another in a grip region 6 in a manner such that they may be moved apart in the direction X. At the same time, the spatulas 2 and 4 are either moved such that they constantly extend parallel to one another or are pivoted apart about rotation axes in the grip region 6 so that the distal ends of the spatulas 2 and 4, i.e. the ends opposed to the grip region, are distanced further to one another in the direction X. The two spatulas 2 and 4 in each case have an essentially U-shaped cross section (see FIG. 3), and together enclose a working space or working channel 8 through which one may introduce auxiliary instruments for an operation. If the two spatulas 2 and 4 are moved apart in the direction X, the working channel 8 is enlarged accordingly in order to create a larger working space for an operation.

According to the invention, in each case two tabs, 10, 12 are formed on each longitudinal side of each spatula 2, 4 (see FIG. 3). At the same time the tabs 10, proceeding from the spatula, extend beyond the middle plane M in the direction of the spatula 2. The tabs 12, proceeding from the spatula 2, extend beyond the middle plane in the direction of spatula 4. The tabs 10 and the tabs 12 (shown dashed) in each case are spaced from one another in the longitudinal direction of the spatulas 2, 4, i.e., in a direction parallel to the middle plane M and normal to the direction X, so that a free space 14 remains between the projections or tabs 10, 12, which improves the view to laterally lying tissue parts. The tabs in the longitudinal direction of the spatula are arranged essentially in the middle region of the spatulas so that the gaps are also not covered distally or proximally of the tabs, and the gaps permit a good view to lateral tissue parts.

The tabs 10 and 12 extend in planes lying parallel to one another and overlap one another (see FIG. 3). At the same time the tabs 10, 12 extend preferably essentially parallel to the direction X, so that the tabs 10 bear on the outer sides of the tabs 12 or extend at a slight distance parallel to these, if the two spatulas 2 and 4 are moved apart (see FIG. 2). The tabs 10 and 12 in the direction X, preferably in each case, have such lengths that even in the condition in which the spatulas 2 and 4 are moved the furthest apart, the gap 9 formed between the spatulas 2 and 4 is completely covered or bridged in the X-direction by the tabs 10 and 12. In this manner, two continuously closed webs between the spatulas 2 and 4 are formed by the tabs 10 and 12, even when these spatulas are located in the position furthest apart from one another, so that a penetration of soft parts or other tissue parts through the lateral gap into the working space 8 may be prevented. The tabs 10, 12 are in each case preferably formed as one piece with the side walling of the spatula 2, 4. In the direction of the respective other spatula the tabs 10, 12 form projecting extensions of the side parts of the spatulas 2 and 4. In this manner, the spatulas 2 and 4 together with the respective projections 10 and 12 may be manufactured easily as one piece from a (sheet) plating blank by way of non-cutting shaping. Furthermore, on the whole, a more compact design of the laryngoscope is made possible.

FIG. 2 shows the laryngoscope according to FIG. 1 in the spread condition, in which the two spatulas 2 and 4 lie further apart from one another, so that gaps 9 extending along the two longitudinal sides of the laryngoscope arise or increase. Even in this spread condition the tabs 10 and 12 still overlap in the region of their outer ends, so that the gaps are completely bridged in a direction normal to the longitudinal axis or to the middle plane M, in order to prevent a penetration of tissue parts. The gap 9 remains free and the free space 14 remains free laterally and between the tabs 10 and 12, so that a good lateral view remains ensured. If the two spatulas 2 and 4 are spread further beyond a certain spreading, the tabs 10 and 12 no longer overlap, but nevertheless continue to bridge or cover a large region of the gap 9 in the transverse direction, so that a penetration of tissue parts into the gaps may be still be prevented.

Even with a large spacing of the spatulas 2 and 4 to one another, the projections 10 and 12 may also bridge the lateral gap, such that no tissue may penetrate into the intermediate space between the spatulas 2 and 4. The projections or tabs 10 and 12, at the same time however, only cover very small lateral regions of the gap 9 arising between the spatulas 2 and 4, so that the lateral view is hardly restricted at all. The tabs 10, 12, which have been described here with the example of a gap 9, are correspondingly formed on the oppositely lying longitudinal gap 9 between the spatulas 2, 4, so that the working channel is protected on both sides from penetration of tissue.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

The invention claimed is:

1. A spreading laryngoscope comprising two spatulas (2,4) lying opposite one another and able to be moved apart, each spatula (2,4) having two longitudinal sides, at least one of the two spatulas (2, 4) having on each longitudinal side thereof at least one projecting tab (10, 12), the at least one projecting tab (10, 12) on each longitudinal side projecting from the respective longitudinal side of the one spatula (2, 4), extending to the opposite-lying spatula (2, 4), and being rigidly connected to the spatula (2, 4) from which it projects, wherein the at least one projecting tab (10, 12) does not extend over a whole longitudinal side in a longitudinal direction.

2. The spreading laryngoscope according to claim 1, wherein each of the two spatulas (2, 4) has on each longitudinal side thereof at least one projecting tab (10, 12), each of the at least one projecting tab (10, 12) projecting from the respective longitudinal sides of each spatula (2, 4), extending to the opposite-lying spatula (2, 4), and being rigidly connected to the spatula (2, 4) from which it projects.

3. The spreading laryngoscope according to claim 2, wherein the tabs (10, 12) on each of the two spatulas (2, 4) are arranged lying opposite one another in a manner such that one tab (10, 12) on a first spatula (2, 4) overlaps with a tab (10, 12) on a second spatula (2, 4) at least in a non-spread condition of the laryngoscope.

4. The spreading laryngoscope according to claim 2, wherein the tabs (10, 12) are designed such that in a spread condition of the laryngoscope at least one tab (10, 12) on a first spatula (2, 4) overlaps with at least one tab (10, 12) on a second spatula (2, 4).

5. The spreading laryngoscope according to claim 1, wherein the at least one tab (10, 12) on each side extends essentially normal to a main surface of the respective spatulas (2, 4).

6. The spreading laryngoscope according to claim 1, wherein each of the two spatulas (2, 4) has on each longitudinal side thereof two tabs (10, 12) which in a non-spread condition of the laryngoscope overlap with two oppositely lying tabs (10, 12) on the respective other spatula (2, 4).

7. The spreading laryngoscope according to claim 6, wherein the two tabs (10, 12) on each longitudinal side of each spatula (2, 4) are spaced from one another in the longitudinal direction of the spatula (2, 4).

8. The spreading laryngoscope according to claim 1, wherein the at least one tab (10, 12) on each side is formed as one piece with the respective spatula (2, 4).

9. The spreading laryngoscope according to claim 1, wherein the two spatulas (2, 4) are able to be moved apart while the spatulas extend parallel to one another.

10. The spreading laryngoscope according to claim 1, wherein the two spatulas (2, 4) together enclose a working channel (8) for receiving auxiliary operation instruments.

11. The spreading laryngoscope according to claim 1, wherein the at least one projecting tab (10, 12) is arranged essentially in a middle region in a longitudinal direction of the longitudinal side.

* * * * *